US007872104B2

United States Patent
Pettersson et al.

(10) Patent No.: US 7,872,104 B2
(45) Date of Patent: Jan. 18, 2011

(54) ANTIBODY, IMMUNOASSAY AND METHOD FOR PROSTATE CANCER DETECTION

(75) Inventors: Kim Pettersson, Turku (FI); Hans Lilja, Skanör (SE); Timo Lövgren, Turku (FI); Pauliina Niemelä, Turku (FI)

(73) Assignee: Arctic Partners Oy AB, Turku (FI)

( * ) Notice: Subject to any disclaimer, the term of this patent is extended or adjusted under 35 U.S.C. 154(b) by 481 days.

(21) Appl. No.: 10/381,132

(22) PCT Filed: Sep. 26, 2001

(86) PCT No.: PCT/FI01/00834

§ 371 (c)(1),
(2), (4) Date: Jul. 21, 2003

(87) PCT Pub. No.: WO02/27323

PCT Pub. Date: Apr. 4, 2002

(65) Prior Publication Data

US 2004/0101914 A1    May 27, 2004

(30) Foreign Application Priority Data

Sep. 27, 2000   (FI) ................................. 20002127

(51) Int. Cl.
*C07K 16/00* (2006.01)
*C07K 17/00* (2006.01)
*C12P 21/08* (2006.01)
*G01N 33/53* (2006.01)
*G01N 33/00* (2006.01)

(52) U.S. Cl. .............................. 530/388.1; 530/388.25; 530/388.8; 530/388.85; 530/391.1; 530/391.3; 435/7.1; 435/7.92

(58) Field of Classification Search ........................ None
See application file for complete search history.

(56) References Cited

U.S. PATENT DOCUMENTS

| 5,858,685 A | 1/1999 | Stamey et al. |
| 6,143,509 A * | 11/2000 | Dowell et al. .............. 435/7.23 |
| 6,423,503 B1 * | 7/2002 | Mikolajczyk et al. ...... 435/7.23 |
| 6,482,599 B1 | 11/2002 | Mikolajczyk et al. |
| 7,211,397 B2 | 5/2007 | Mikolajczyk et al. |
| 7,659,073 B2 | 2/2010 | Mikolajczyk et al. |
| 2002/0045198 A1 * | 4/2002 | Mikolajczyk et al. ...... 435/7.23 |

FOREIGN PATENT DOCUMENTS

| WO | WO 98/49323 A1 | 11/1998 |
| WO | WO 00/66718 A1 | 11/2000 |

OTHER PUBLICATIONS

Chu, LF et al. Journal of Urology 161: 2009-2012, 1999.*
Wang, TJ et al. Eur. J. Biochem. 267: 4040-4045, 2000.*
Nurmikko et al. Clinical Chemistry 46(10): 1610-1618, 2000.*
Wang, TJ et al. Tumor Biology 20, Suppl. 1, 79-85, 1999.*
Chen et al (J. Urol., 157: 2166-2170, 1997).*
Harlow and Lane (Antibodies, a Laboratory Manual, Cold Spring Harbor Laboratory Press, 1988, p. 141-142).*
Leinonen, J. et al. (1999). "Reactivity of 77 Antibodies to Prostate-Specific Antigen with Isoenzymes and Complexes of Prostate-Specific Antigen," *Tumor Biol.* 20 (Suppl. 1), pp. 28-34.
Paus, E. et al. (1999). "Epitope Mapping and Affinity Estimation of 83 Antibodies Against Prostate-Specific Antigen," *Tumor Biol.* 20 (Suppl. 1), pp. 52-69.
Nurmikko, P. et al. (2000). "Production and Characterization of Novel Anti-Prostate-Specific Antigen (PSA) Monoclonal Antibodies That Do Not Detect Internally Cleaved Lys145-Lys146 Inactive PSA," *Clinical Chem.* 46:10, pp. 1610-1618.
Wang, T.J. et al. (2000). "Benign Prostatic Hyperplasia-Associated Prostate-Specific Antigen (BPSA) Shows Unique Immunoreactivity With Anti-PSA Monoclonal Antibodies," *Eur. J. Biochem.* 267, pp. 4040-4045.

* cited by examiner

*Primary Examiner*—Peter J Reddig
(74) *Attorney, Agent, or Firm*—Rothwell, Figg, Ernst & Manbeck pc

(57) ABSTRACT

This invention concerns an antibody which binds with high affinity to human single-chain intact, i.e. not internally cleaved, mature and/or zymogen forms of prostate specific antigen (SCINT PSA). The antibody does not bind to a nicked PSA (PSA-N), wherein said PSA-N has been formed by internal peptide bond cleavage(s) of SCINT PSA resulting in two-chain or multi-chain PSA. This invention further concerns an immunoassay and a method for differentiating patients with cancer of the prostate (PCa) from patients with benign prostatic hyperplasia (BPH) and/or healthy male subjects without PCa, patients with aggressive PCa from patients with indolent PCa and/or patients with clinically localized and/or organ confined PCa from patients with extraprostatic extension of PCa and/or PCa with metastatic spread to lymph nodes or bone marrow using said antibody.

6 Claims, 10 Drawing Sheets

SEQUENCE LISTING

<160> NUMBER OF SEQ ID NOS: 6

<210> SEQ ID NO 1
<211> LENGTH: 15
<212> TYPE: PRT
<213> ORGANISM: Homo sapiens

<400> SEQUENCE: 1

Ala Ser Gly Trp Gly Ser Ile Glu Pro Glu Glu Phe Leu Thr Pro
1               5                   10                  15

<210> SEQ ID NO 2
<211> LENGTH: 16
<212> TYPE: PRT
<213> ORGANISM: Homo sapiens

<400> SEQUENCE: 2

Ser Ile Glu Pro Glu Glu Phe Thr Leu Thr Pro Lys Lys Leu Gln Cys
1               5                   10                  15

<210> SEQ ID NO 3
<211> LENGTH: 10
<212> TYPE: PRT
<213> ORGANISM: Homo sapiens

<400> SEQUENCE: 3

Ser Ile Glu Pro Glu Glu Phe Leu Thr Pro
1               5                   10

<210> SEQ ID NO 4
<211> LENGTH: 13
<212> TYPE: PRT
<213> ORGANISM: Homo sapiens

<400> SEQUENCE: 4

Tyr Arg Lys Trp Ile Lys Asp Thr Ile Val Ala Asn Pro
1               5                   10

<210> SEQ ID NO 5
<211> LENGTH: 15
<212> TYPE: PRT
<213> ORGANISM: Homo sapiens

<400> SEQUENCE: 5

Arg Pro Ser Leu Tyr Thr Lys Val Val His Tyr Arg Lys Trp Ile
1               5                   10                  15

<210> SEQ ID NO 6
<211> LENGTH: 14
<212> TYPE: PRT
<213> ORGANISM: Homo sapiens

<400> SEQUENCE: 6

Ala Pro Leu Ile Leu Ser Arg Ile Val Gly Gly Trp Glu Cys
1               5                   10

ANTIBODY, IMMUNOASSAY AND METHOD FOR PROSTATE CANCER DETECTION

CROSS-REFERENCE TO RELATED APPLICATION

Figure 1A:
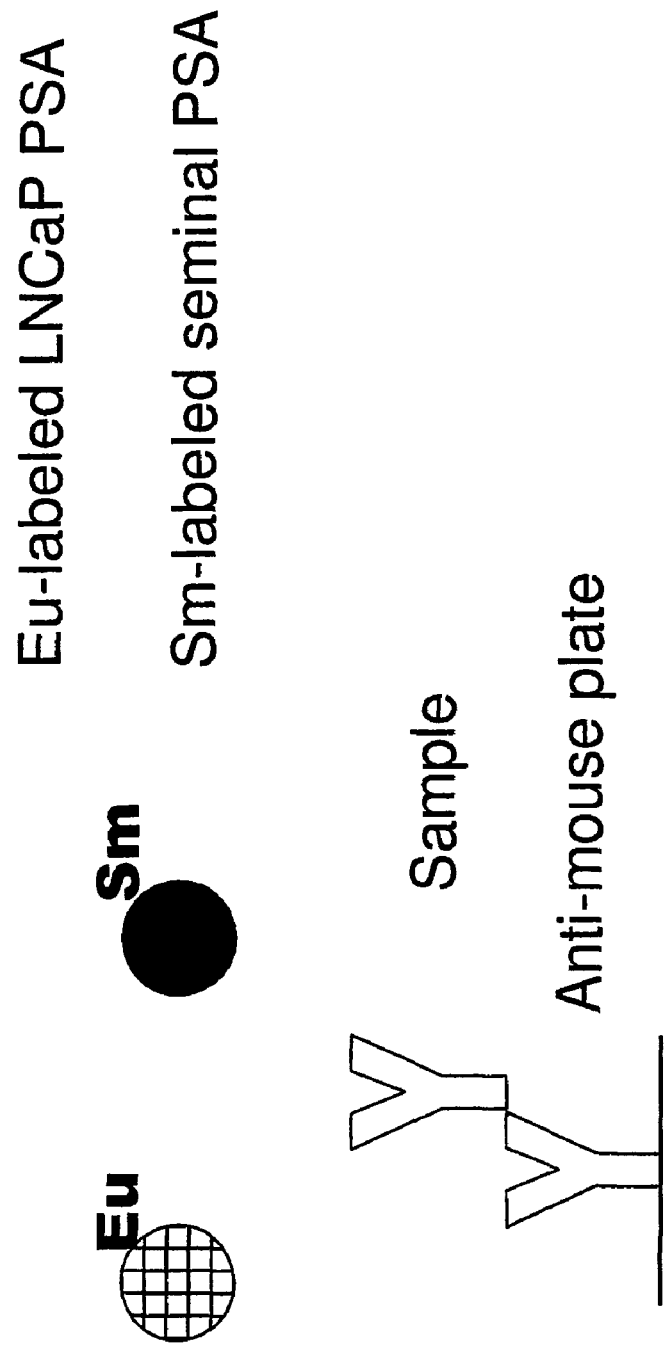
Figure 1B:
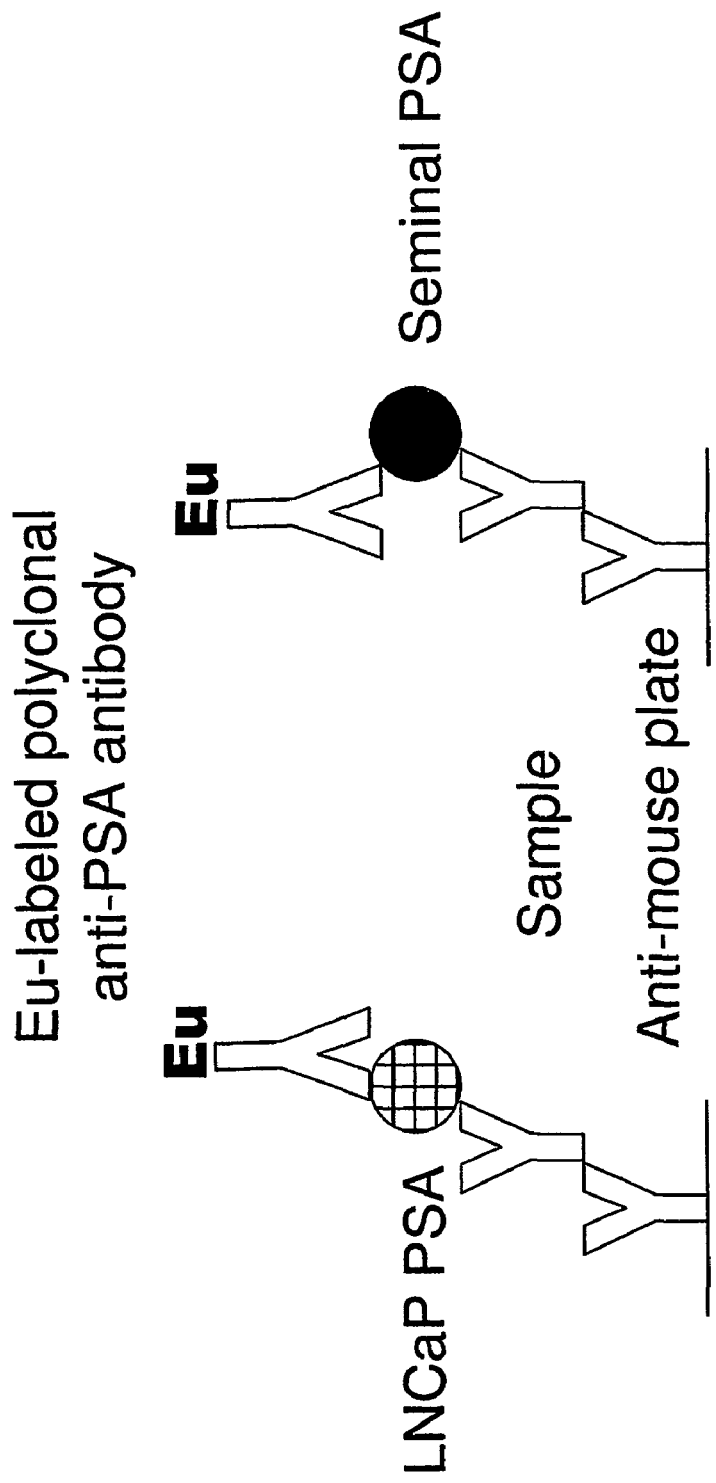
Figure 1C:
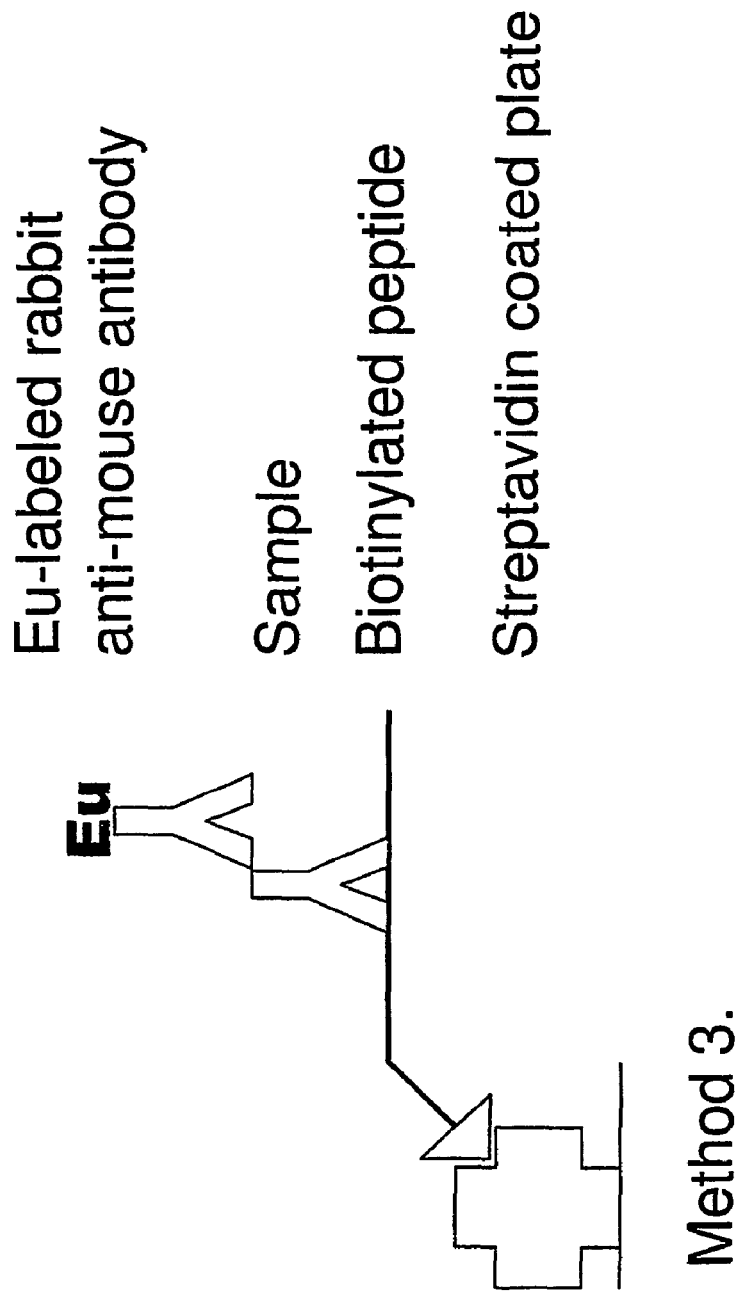
Figure 1D:
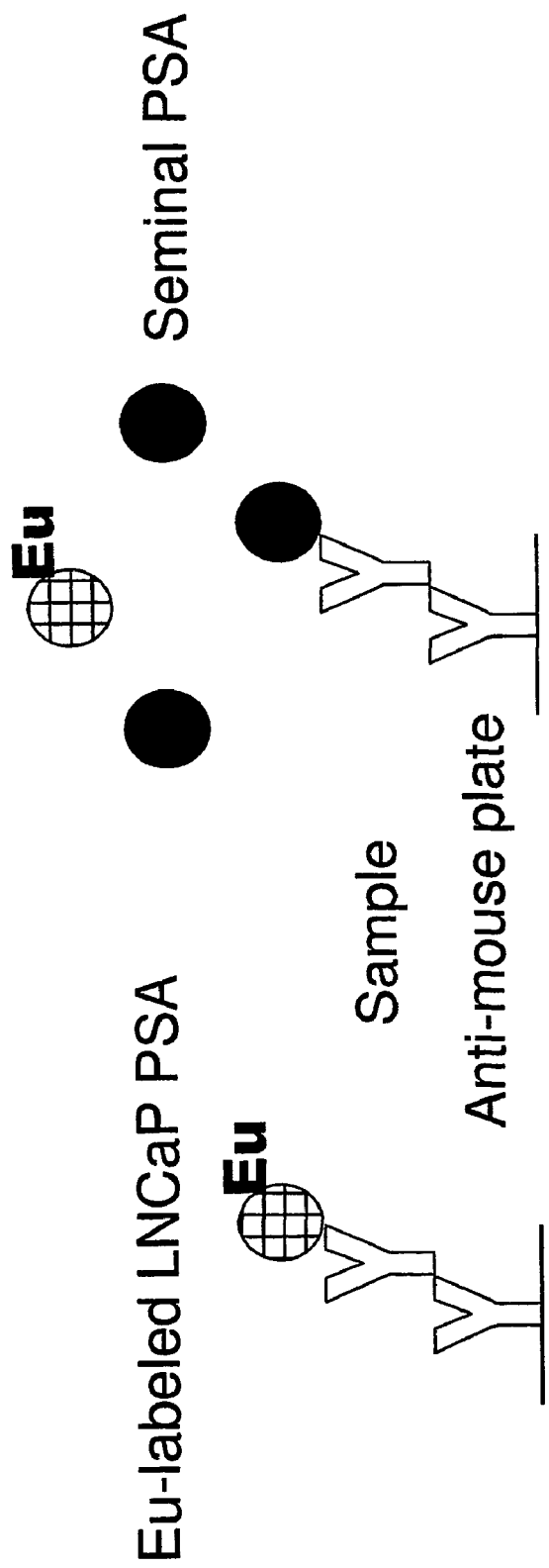

The present application is a national stage filing under 35 U.S.C. §371 of PCT/FI01/00834 filed on 26 Sep. 2001 and claims priority under 35 U.S.C. §119 to Finland patent application number 2000-127 filed on 27 Sep. 2000.

SEQUENCE SUBMISSION

The present application includes a Sequence Listing filed in electronic format. The Sequence Listing is entitled "sequencelisting.txt", was created on 26 Oct. 2009, and is 1,543 bytes in size. The information in the electronic format of the Sequence Listing is part of the present application and is incorporated herein by reference in its entirety.

FIELD OF INVENTION

This invention relates to high affinity immunoreagents which are specific for the single-chain, intact (i.e. not internally-cleaved) form(s) of prostate specific antigen (PSA or hK3). It also relates to the discrimination of prostate cancer from healthy asymptomatic men or benign prostatic conditions by an analytically sensitive immunoassay, employing the aforementioned immunoreagents, for the specific determination of the single-chain, intact (not internally cleaved) form(s) of free, noncomplexed PSA (free SCINT PSA), or by combining the result from this immunoassay with immunoassays measuring any other forms of the prostatic kallikreins, PSA or hK2, either by forming various ratios of these or by combining them with other means, e.g. using logistic regression and/or artificial neural networks. The invention may be used for detection of prostate cancer both in screening of asymptomatic individuals as well as in distinguishing cancer from benign conditions in men presenting with clinical symptoms (e.g. lower urinary tract symptoms, LUTS). Further, the invention may be used to improve the staging and grading of prostate cancer as well as to provide improved means to detect recurrence of cancer at early stage and provide improved means to monitor therapeutic response at various stages of disease. Suitable biological specimens for the immunoassay determinations are mainly serum, plasma or whole blood samples, but the invention may also be applied to other biological fluids such as urine and seminal fluid samples.

BACKGROUND

The publications and other materials used herein to illuminate the background of the invention, and in particular, cases to provide additional details respecting the practice, are incorporated by reference.

Prostate-specific antigen (PSA; also designated hK3) and human glandular kallikrein 2 (hK2) are two closely related serine proteases highly expressed, predominantly in prostatic tissue. [Wang et al. *Invest Urol* 1979; 17:159-163, Lilja *J Clin Invest* 1985; 76:1899-1903, Chapdelaine et al. *FEBS Lett* 1988; 236:205-208]. The PSA gene is located on the long arm of chromosome 19 and has >84% nucleotide sequence identity with hK2. The two proteins also show extensive similarity in amino-acid sequence (79%) but the expression rates are quite different (hK2 mRNA levels amount to ~10-20% of PSA mRNA levels) [Schedlich et al. *DNA* 1987; 6:429-437]. PSA is synthesized as a 261 amino acid preproform from which the 17-21 amino acid signal peptide is cleaved and released in the secretion process. The remaining zymogen form of PSA is activated to an active serine protease by cleavage of 3-7 amino acid propeptide [Lövgren et al. *Biochem. Biophys. Res. Comm.* 1997; 238; 549-555]. Recently, recombinant hK2 was shown to convert in vitro inactive recombinant proPSA into active mature PSA [Lövgren et al. *Biochem Biophys Res Commun* 1997; 238:549-555, Takayama et al. *J Biol Chem* 1997; 272:21582-21588, Kumar et al. *Cancer Res* 1997; 57:3111-3114]. Therefore, hK2 is likely a physiological activator of proPSA. Enzymatically active PSA is secreted into seminal fluid at high concentrations (0.2-5 mg/mL) [Christensson et al. *Eur J Biochem* 1990; 194:755-763, Ahlgren et al. 1995 *J Androl* 16:491-498]. In semen, PSA degrades the seminal vesicle derived gel-forming proteins semenogelin I and II, causing liquefaction of semen and release of progressively motile spermatozoa [Lilja *J Clin Invest* 1985; 76:1899-1903]. The action of PSA generates hydrolysis of peptide bonds, mainly C-terminal, of certain tyrosine- and glutamine residues in semenogelin I and II [Malm et al. *The Prostate* 2000; In press]. By contrast, hK2 generates distinctly different cleavage patterns in semenogelin I and II compared to those generated by the action of PSA, though it is presently unclear whether the hK2 action on the gel proteins has physiological significance [Lövgren et al. *Eur. J. Biochem.* 1999; 262; 781-789].

Enzymatically active PSA has been shown to manifest unique substrate specificity with limited similarity to chymotrypsin-like proteases [Lilja et al. *J Biol Chem* 1989; 264: 1894-1900 Christensson et al. *Eur J Biochem* 1990; 194:755-763, Malm et al. *The Prostate* 2000; In press]. The active single-chain form of PSA forms stable covalent complexes with several extracellular protease inhibitors, such as $\alpha_1$-antichymotrypsin (ACT), $\alpha_2$-macroglobulin (AMG), pregnancy-zone protein (PZP), protein C inhibitor (PCI), and $\alpha_1$-antitrypsin (API) [Christensson et al. *Eur J Biochem* 1990; 194:755-763, Stenman et al. *Cancer Res* 1991; 51:222-226, España et al. *Thromb Res* 1991; 64:309-320, Christensson and Lilja *Eur J Biochem* 1994; 220:45-53, Zhang et al. *Prostate* 1997; 33:87-96]. In blood, the predominant immunodetectable form of PSA is covalently linked in complex with ACT and only a minor fraction is in a free, noncomplexed form (PSA-F) [Stenman et al. *Cancer Res* 1991; 51:222-226, Lilja et al. *Clin Chem* 1991; 37:1618-1625].

LNCaP (lymph node cancer of the prostate) is a human metastatic prostate adenocarcinoma cell line that was isolated in 1977 from a needle aspiration biopsy of a patient with confirmed metastatic prostate cancer. Various forms of free PSA have been found in spent cell culture medium of LNCaP cells. Corey et al. and Väisänen et al. reported LNCaP cells to produce zymogen forms of PSA (proPSA) and a mature intact form of PSA. However, the LNCaP cells do not appear to produce any internally cleaved forms of PSA, by contrast to PSA from seminal fluid which partially occurs as enzymatically inactive forms due to internally cleavage(s) mainly between $Lys_{145}$ and $Lys_{146}$ [Christensson et al. *Eur J Biochem* 1990; 194:755-763]. The zymogen form of PSA has been found also in serum of patients with prostate cancer. Since the zymogen form of PSA is enzymatically inactive, it cannot form complexes with serpins and is likely to remain in a free form in the circulation. There are also other, contradictory reports on the nature of the free PSA form occurring in serum, stating that it is a cleaved, inactive form resulting from internal cleavage(s) or that it represents an unclipped mature but enzymatically inactive form of PSA.

The incidence of prostate cancer has increased during the last decade mainly due to prolonged lifetime and increased screening. This fact underlines the need of improved diagnostic approaches and new treatments. Analysis of PSA in serum is well established in the diagnosis and monitoring of prostate-cancer (PCa) patients [*Oesterling J Urol* 1991; 145:907-923]. However, raised serum concentrations of PSA are also found in patients with other prostatic diseases, for instance benign hyperplasia of the prostate (BPH) [Hudson et al. *J Urol* 1989; 142:1011-1017]. The discovery of several different molecular forms of PSA in serum have significantly improved the specificity of diagnosis and monitoring for PCa. Patients with BPH have higher proportions of free-to-total PSA (i.e. PSA-F+PSA-ACT+other quantitatively less important PSA-serpin complexes), or free-to-complexed PSA in serum than patients with PCa. This has resulted in the use of free-to-total PSA (also called percent free PSA) to distinguish between BPH and PCa in men with moderately elevated PSA levels in serum [Stenman et al. *Cancer Res* 1991; 51:222-226, Christensson et al. *J Urol* 1993; 150:100-105]. Although this has improved the specificity for PCa, there is still considerable overlap between the two groups of men and therefore a great need for markers, which provide further improved discrimination of men with cancer from normal men and men with benign conditions.

Immunizations of mice with purified PSA have resulted in generation of monoclonal antibodies against PSA and hK2. Many monoclonal antibodies cross react with PSA and hK2 due to the extensive identity in primary structure of the two proteins. However, specific immunoassays that selectively measure free PSA, complexed PSA and hK2 have been developed by us and others. At present, there are no immunoassays available that specifically recognize various candidate forms of free PSA.

OBJECTIVE AND SUMMARY

The object of the present invention is to enable the determination of human single-chain intact, i.e. not internally cleaved, mature and/or zymogen forms of prostate specific antigen (SCINT PSA) from a sample containing such antigen.

Another objective of the present invention is to provide an immunoassay for the quantitative determination of SCINT PSA in a sample containing such antigen.

A further objective of the present invention is to provide a method for differentiating patients with cancer of the prostate (PCa) from patients with benign prostatic hyperplasia (BPH) and/or healthy male subjects without PCa, patients with aggressive PCa from patients with indolent PCa, and/or patients with clinically localized and/or confined PCa from patients with extraprostatic extension of PCa and/or PCa with metastatic spread to lymph nodes or bone marrow.

The present invention thus concerns an antibody, wherein said antibody does bind with high affinity to human single-chain intact, i.e. not internally cleaved, mature and/or zymogen forms of prostate specific antigen (SCINT PSA). The antibody, obtainable through immunization with an uncleaved form of PSA and selected by its differential reactivity with the intact and internally cleaved forms, does not bind to a nicked PSA (PSA-N), wherein said PSA-N has been formed by internal peptide bond cleavage(s) of SCINT PSA resulting in two-chain or multi-chain PSA.

The present invention also concerns an immunoassay for quantitative determination, in a sample, of a human single-chain intact, i.e. not internally cleaved, mature and/or zymogen forms of prostate specific antigen (SCINT PSA), or alternatively nicked PSA forms (PSA-N), wherein said PSA-N has been formed by internal cleavage(s) of SCINT PSA resulting in two-chain or multi-chain prostate specific antigen (PSA) forms, which SCINT PSA or PSA-N may occur both free and/or complexed. The immunoassay uses an antibody, which does bind with high affinity to said SCINT PSA, but does not bind to PSA-N.

The present invention further concerns a method for differentiating i) patients with cancer of the prostate (PCa) from patients with benign prostatic hyperplasia (BPH) and/or healthy male subjects without PCa, ii) patients with aggressive PCa from patients with indolent PCa and/or iii) patients with clinically localized and/or organ confined PCa from patients with extraprostatic extension of PCa and/or PCa with metastatic spread to lymph nodes or bone marrow.

The method comprises the following steps a) human single-chain intact, i.e. not internally cleaved, prostate specific antigen (SCINT PSA) free and/or complexed is determined, b) a marker value, which is a function of determined SCINT PSA is established, and c) the established marker value is used for differentiation of said patients.

BRIEF DESCRIPTION DRAWINGS

FIGS. 1*a*-1*d*. Four screening methods used in the search for novel anti-PSA antibodies.

Figure 2:
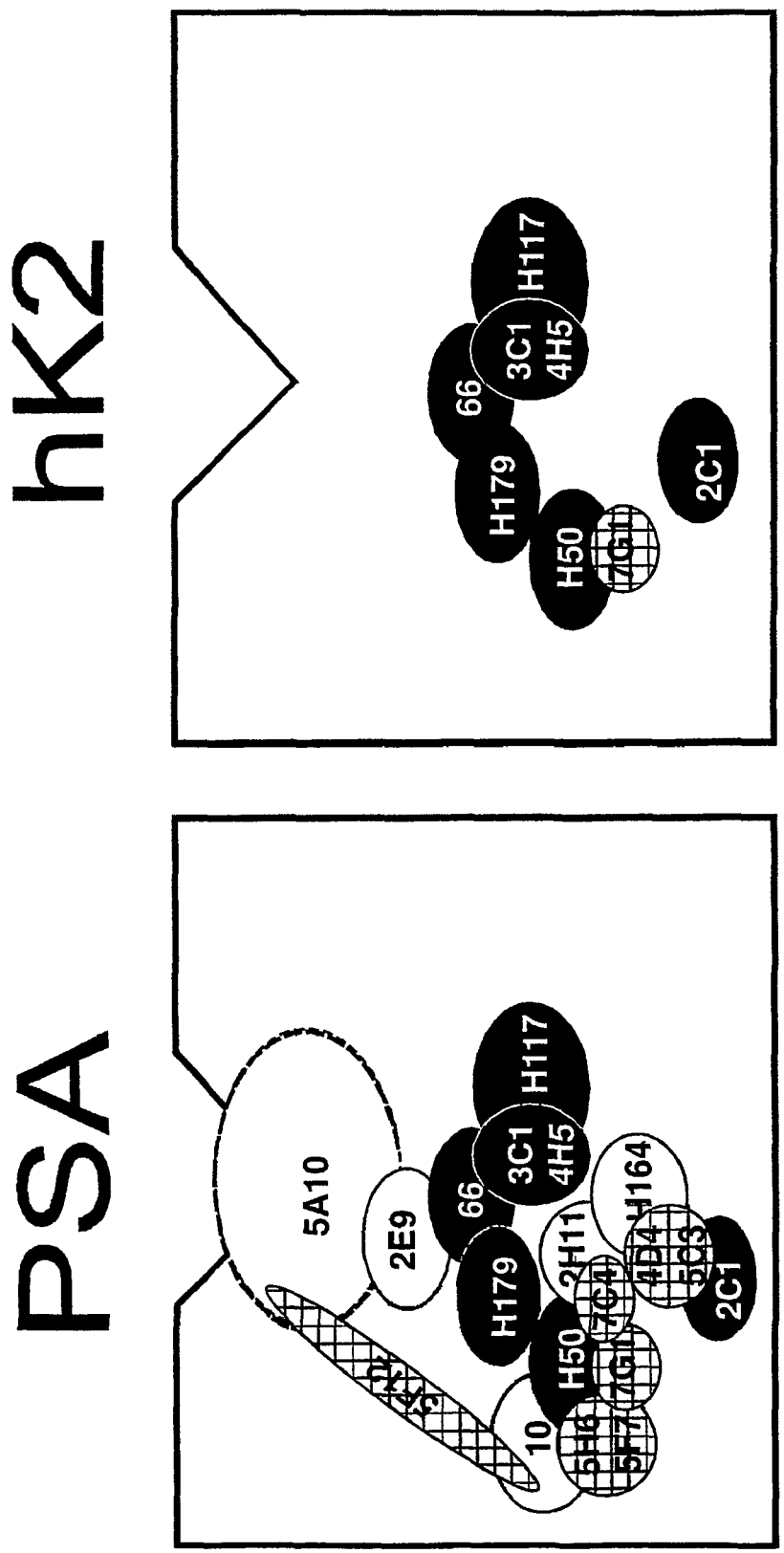

FIG. 2. Epitope mapping of novel and previously characterized Mabs in relation to each other in a 2-D model of PSA. Overlapping circles indicate that the Mabs cannot sandwich each other. Touching circles indicate detectable interference (competition) in binding to PSA, whereas nonoverlapping circles indicate that the Mabs detect independent epitopes and can sandwich other antibodies in the other nonoverlapping circles. Antibodies located in white circles are specific for PSA whereas antibodies in black circles cross react with hK2. Antibody circles (cross pattern) denote the novel antibodies developed in this study.

Figure 3:
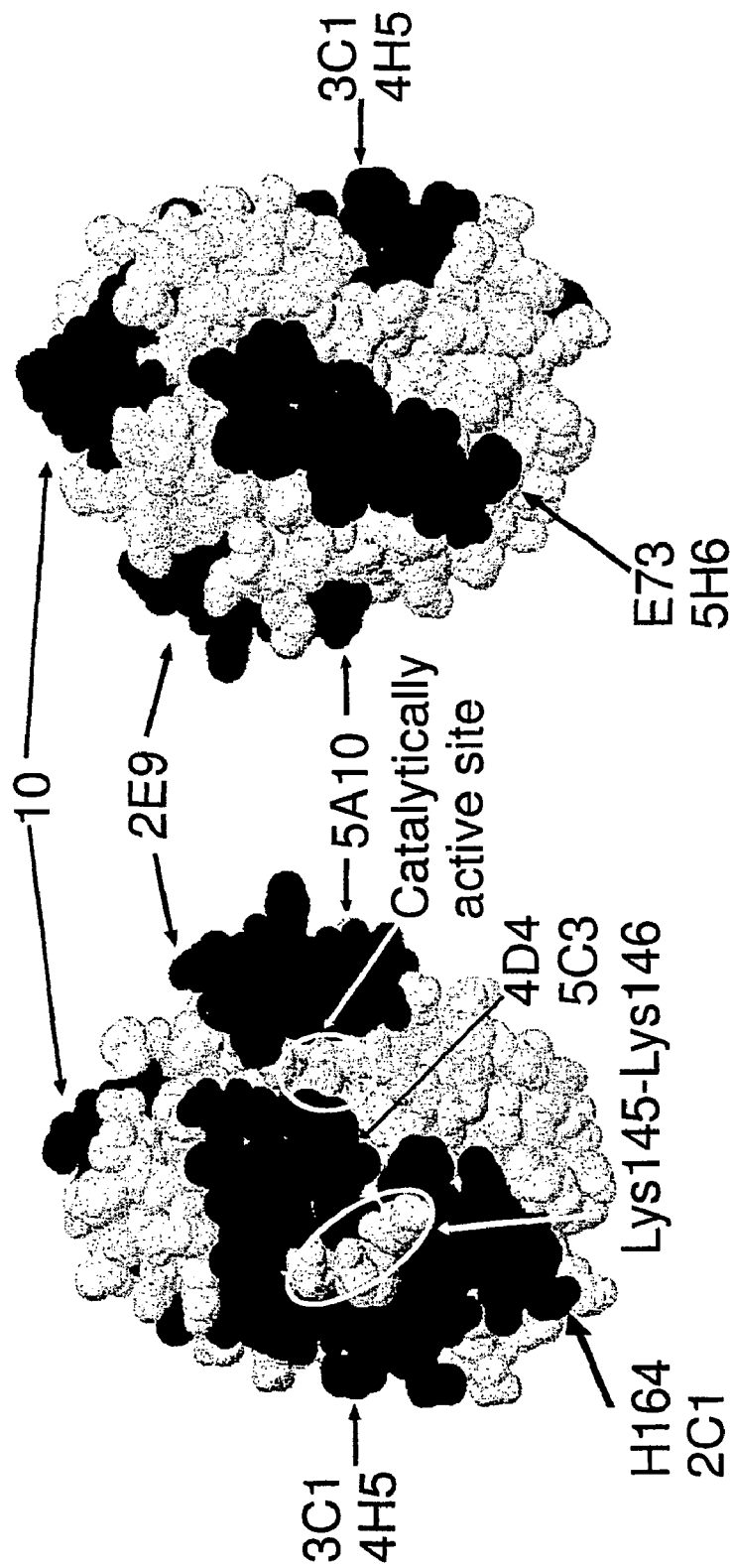

FIG. 3. Epitope groups of PSA in a 3-D model structure. Antibodies that bind to linear peptide sequences are mapped to this model. Seven independent antigenic domains are shown. Mab 5A10 binds to the peptide sequence consisting of amino acids 84-91, Mab 2E9 aa 80-83, Mab 10 aa 150-164, Mab 3C1 and Mab 4H5 aa 1-11 (i.e. aa 3, 5-6, and 8-11), and Mab H164 and Mab 2C1 aa 50-64 as reported previously [Piironen et al. *Protein Science* 1998; 7:259-69]. E73 binds to peptide sequence aa 215-229. The new 5H6 Mab is mapped to an epitope located very close to the epitope of Mab E73, as 5H6 was bound to the adjacent peptide sequence aa 225-237. Mabs 4D4 and 5C3 were bound to peptide sequence 136-144 which is a previously unrecognized antigenic epitope on PSA. The internal cleavage site between Lys145 and Lys146 is also indicated in the figure, as well as the catalytically active site in the vicinity of the Mab 4D4 and Mab 5C3 epitopes.

Figure 4A:
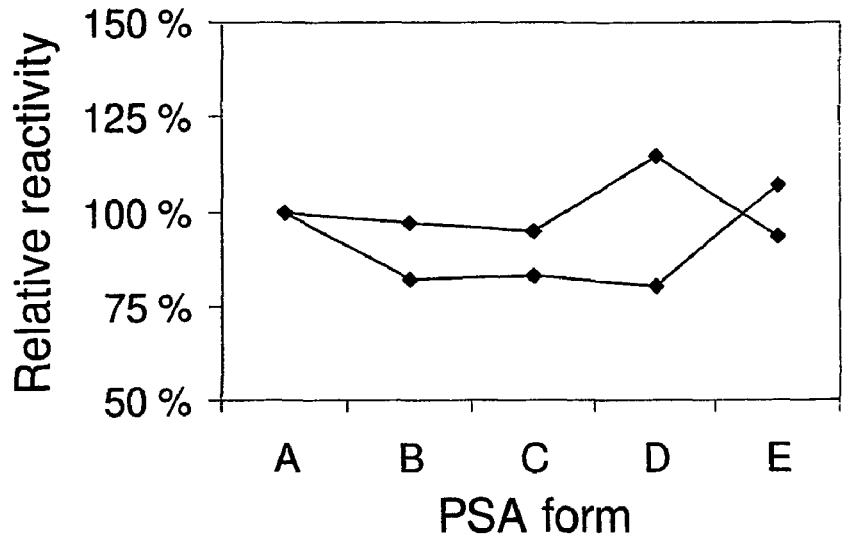
Figure 4A:
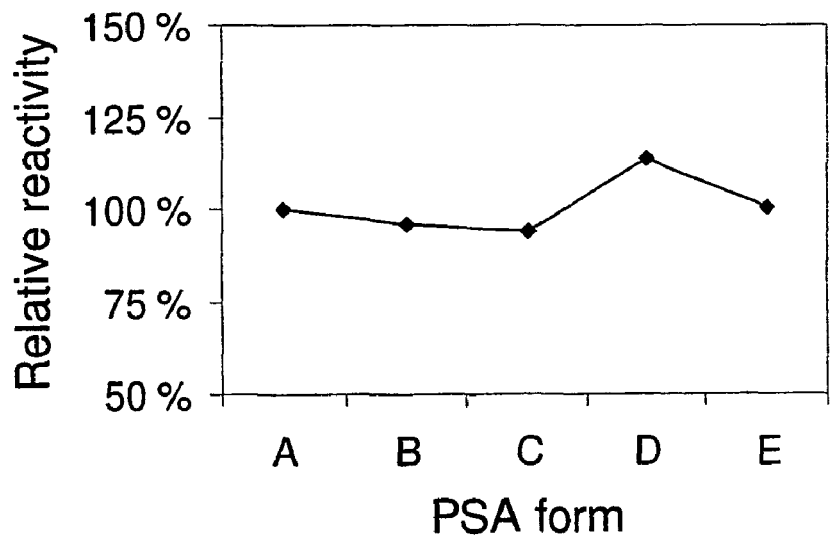
Figure 4B:
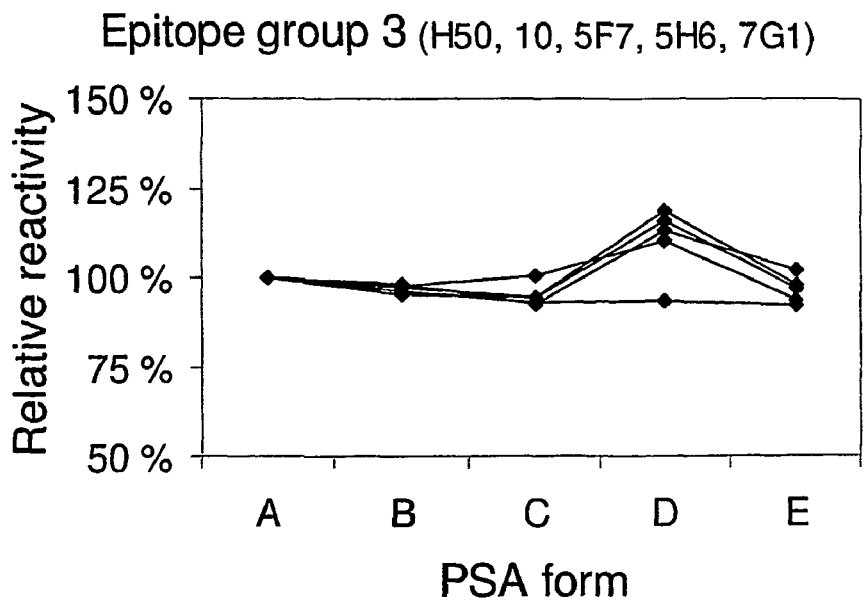
Figure 4B:
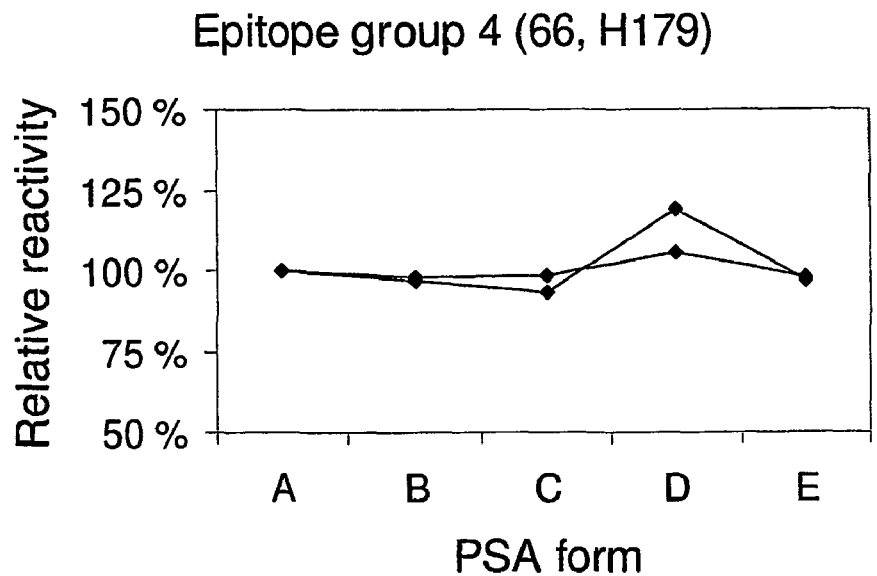
Figure 4C:
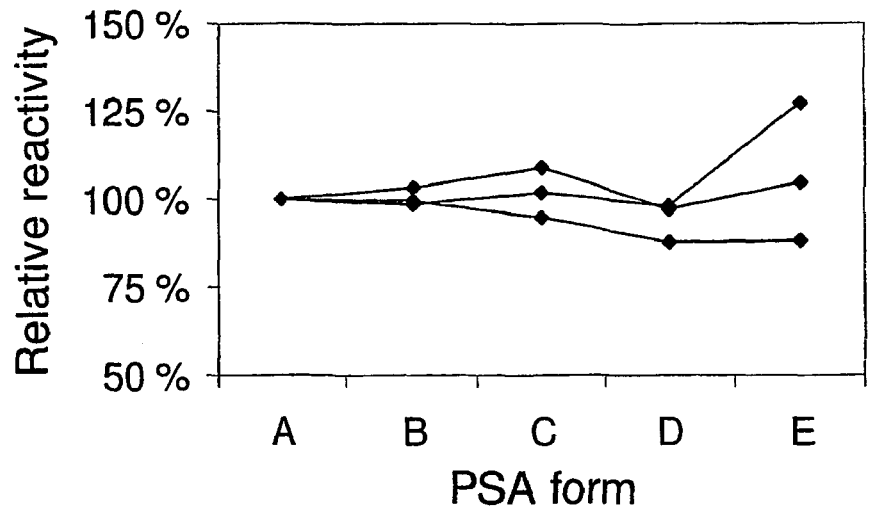
Figure 4C:
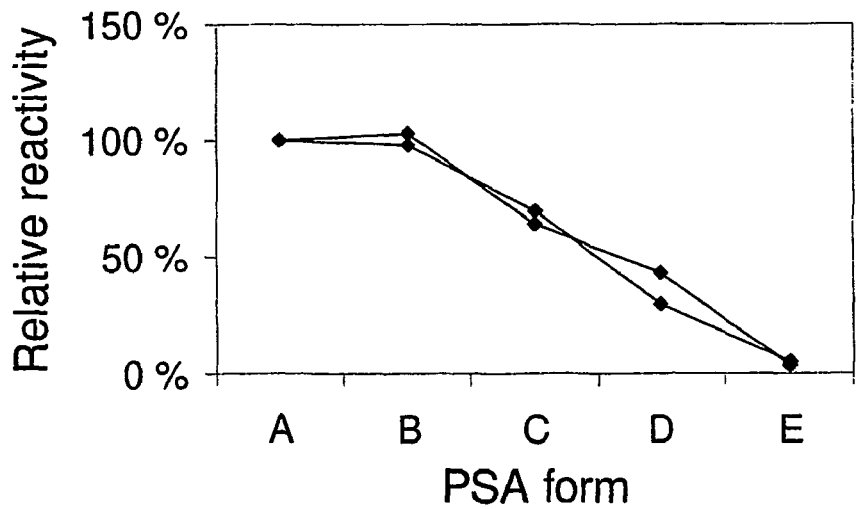

FIGS. 4*a*-4*c*. Reactivity of antibodies with PSA reactivity of each antibody with an isoenzyme was compared to the median reactivity of all antibodies with that isoenzyme. Reactivity with intact isoform A was set as 100%. Antibody groups are numbered 1-5 based on antibody binding regions according to the ISOBM epitope nomenclature. Pools A-E were used 1 ng/well and Eu-Mabs 50 ng/well.

Figure 5:
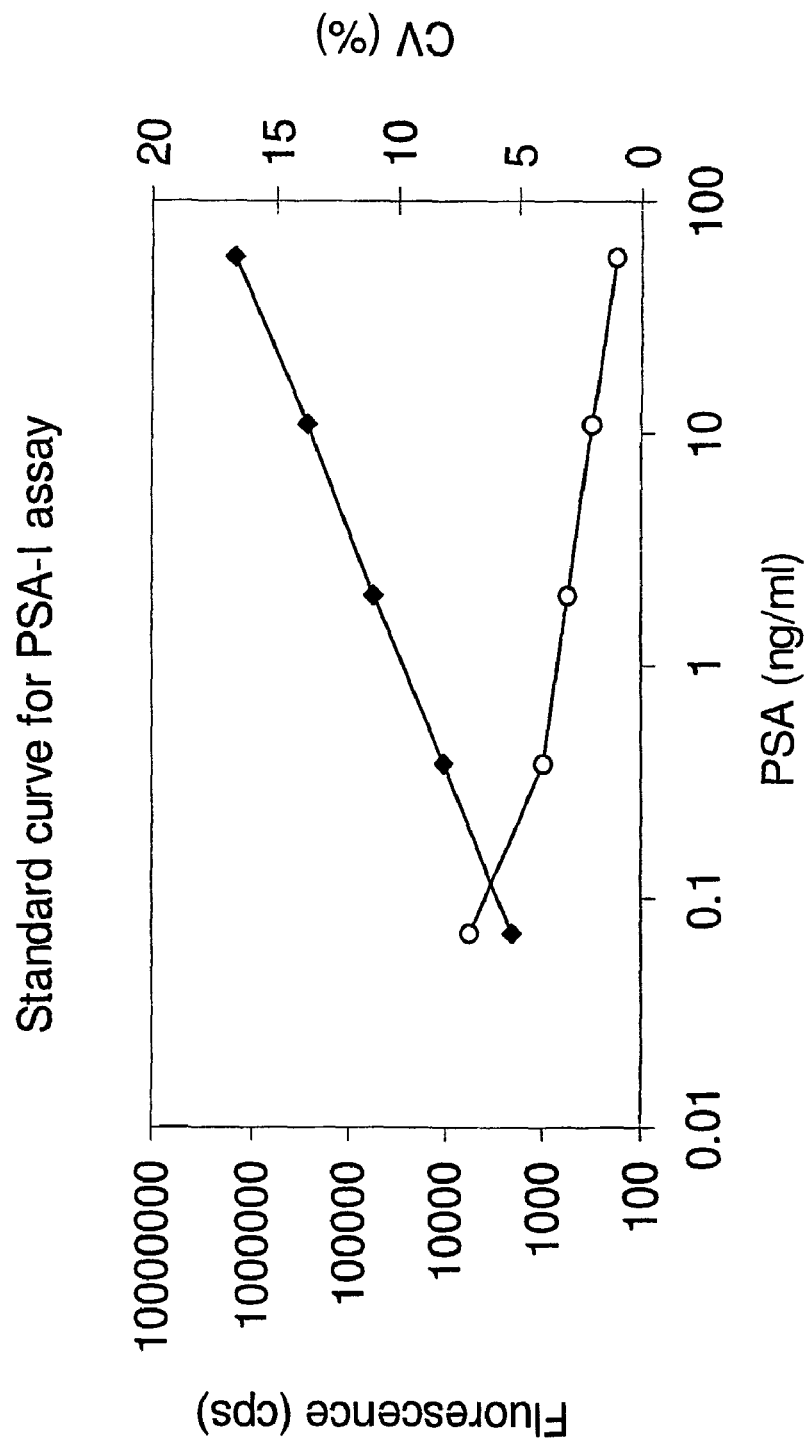

FIG. 5. The free SCINT-PSA assay standard curve.

BRIEF DESCRIPTION OF TABLES

TABLE 1. Summary of the results from immunizations and fusions.

TABLE 2. Summary of antibody characteristics.

TABLE 3. Discrimination of cancers and noncancers using single or combined parameters in the PSA-T range below 5 µg/L. Statistical analysis was performed using the nonparametric Mann-Whitney-U test.

TABLE 4. Discrimination of cancers and noncancers using single or combined parameters in the PSA-T range below 10 µg/L. Statistical analysis was performed using the nonparametric Mann-Whitney-U test.

TABLE 5. Discrimination of cancers and noncancers using single or combined parameters without restrictions as to the concentrations of PSA-T. Statistical analysis was performed using the nonparametric Mann-Whitney-U test.

DETAILED DESCRIPTION OF THE INVENTION

Design and development of analytical procedures to address the nature of the different forms of free PSA could add new discriminatory information to the diagnostics of prostate cancer. An anti-proPSA antibody would enable specific and sensitive measurement of the zymogen forms of the protein. Despite the high immunogenic nature of the LNCaP PSA, we were unable to generate antibodies specific for or with strong preference for the PSA-zymogen, e.g. antibodies which specifically recognizes the entire PSA-propeptide or parts of this propeptide. The aim of this project was to develop anti-PSA antibodies against various PSA forms produced by the metastatic cancer cell line LNCaP and to employ these antibodies in immunoassays to provide specific detection and quantitative measurements of the concentrations of different PSA fractions that may be enzymatically inactive (and therefore unable to form the covalent linkages with the different serpin-type complexing ligands such as ACT, AMG, or API e.g. PSA-zymogen forms {i.e. proPSA}, enzymatically inactive single-chain mature forms, various internally cleaved forms or other inactive forms remaining in noncomplexed form in serum due to as yet unidentified reasons).

We here report:

1. The development and production of monoclonal antibodies that specifically and with high affinity recognize the single-chain, intact (i.e. not internally cleaved) mature and/or zymogen PSA-form(s) but which do not recognize internally cleaved two- or multi-chain forms.

2. Optimization of a highly sensitive two-site immunoassay, using antibodies, which are selectively recognize the single-chain, intact (i.e. not internally cleaved) mature or zymogen form(s) and combined with antibodies which recognized free, noncomplexed PSA to measure the single-chain, intact (i.e. not internally cleaved) mature or zymogen form(s) of free, noncomplexed PSA (free Single-Chain INTact non-complexed PSA or fee SCINT-PSA). The assay is applicable for samples of serum, plasma or whole blood as well as other biological fluids.

3. Application of this assay to a study population (N=281) of serum or plasma samples obtained from asymptomatic men aged 50 to 66 years old initially presenting with a concentration of total PSA of 3 µg/L or more. The diagnosis of PC was based on sextant biopsy. The performance of this assay alone or in combination with other forms of kallikreins (PSA or hK2) to separate noncancers from PC were studied and compared to other established diagnostic procedures.

4. Design of a highly sensitive two-site immunoassay for the measurement of the single-chain intact (i.e. both mature- and zymogen-forms) occurring as both free and complexed PSA-forms. This is accomplished using antibodies which selectively recognize the single-chain, intact (i.e. not internally cleaved) mature and zymogen form(s). These antibodies are combined with independently binding antibodies which recognize both free and complexed PSA-forms with equal affinity (SCINT-PSA). This assay is applicable for samples of serum, plasma or whole blood as well as other biological fluids.

5. Design of a highly sensitive two-site immunoassay which selectively measures internally cleaved PSA-forms independent on whether they occur as free or complexed PSA-forms (i.e. nicked PSA or PSA-N). This assay design first uses a large excess of antibodies which selectively recognize the single-chain, intact (i.e. not internally cleaved) mature and zymogen form(s). This is carried out in order to inhibit or block the binding of the intact single-chain PSA by another antibody which bind PSA at an epitope overlapping with that defined by the first blocking antibody. After addition of such an overlapping antibody (used for detection or capture), a third independently binding antibody suitable as a sandwiching partner to the second antibody is added to complete the immunoreaction. Due to the design of the assay, solely PSA which is internally cleaved at Lys145-Lys146 will be measured independently on whether it occurs in free or complexed forms.

This invention relates to the development of high affinity immunoreagents specific for SCINT-PSA. By employing these high affinity antibodies, the invention also relates to the establishment of very sensitive immunoassays, highly specific for the measurements of the concentration of free SCINT-PSA and SCINT-PSA to be used to discriminate men with prostate cancer from healthy asymptomatic men or those with benign prostatic conditions. The invention may be used for PCa detection both in screening of asymptomatic individuals as well as in distinguishing cancer from benign conditions in men presenting with clinical symptoms (e.g. lower urinary tract symptoms, LUTS). In addition, the invention may be used to improve the staging and grading of prostate cancer as well as to provide improved means to detect recurrency of cancer at early stage and provide improved means to monitor therapeutic response at various stages of disease.

According to the invention, specific monoclonal antibodies can be developed which detect the single-chain, intact (i.e. not internally cleaved) mature and/or zymogen form(s) of PSA with high affinity. More detailed analysis of such antibodies show that they are unable to recognize a two-chain form of PSA presenting with an internal cleavage between Lys145 and Lys146. This form constitutes one commonly occurring nicked (i.e. internally cleaved) form of PSA in seminal plasma as well as in the circulation.

According to the invention, immunoassays which specifically detect free SCINT-PSA can be performed on serum, plasma and whole blood samples as well as on other biological fluids such as urine or seminal plasma obtained from the individuals under investigation. Furthermore the calculated difference between free SCINT-PSA and PSA-F will yet provide another important parameter that of nicked PSA (PSA-N).

As aforementioned, the access to the SCINT-PSA specific monoclonal antibodies also provides an opportunity, described in this invention, to design an immunoassay whereby the nicked PSA can specifically be quantified by completely blocking SCINT-PSA with the help of the SCINT-PSA specific antibodies claimed in this invention, then proceed with detection of the nicked PSA forms through the use of PSA antibodies no longer reactive with the intact free or intact complexed PSA forms. Such a design enables nicked PSA (whether free or complexed) to be measured without the use of free-PSA antibodies.

According to the central findings of this invention, the use of the immunoassay specific for free SCINT-PSA as an efficient tumor marker can be either realized by using free SCINT-PSA or the calculated PSA-N alone or using either of these parameters in combination with any of the different forms of free, complexed, and total PSA and/or hK2 (e.g. total PSA or total hK2, complexed PSA or complexed hK2, any specific protease inhibitor in complex with PSA or any specific protease inhibitor in complex with hK2, total concentrations of free PSA [i.e. single-chain intact mature and zymogen forms+various internally cleaved two- or multi-chain forms] or total concentration of free hK2, and/or various internally cleaved two- or multi-chain forms of free PSA or various internally cleaved two- or multi-chain forms of free hK2).

According to a further aspect of the invention the combination of free SCINT-PSA, SCINT-PSA or PSA-N with other measured forms of PSA can be performed by forming various ratios or algorithms of the measured parameters such as:

the ratio of free SCINT-PSA or PSA-N to total free PSA the ratio of free SCINT-PSA or PSA-N to total PSA the ratio of free SCINT-PSA divided by the total concentration of free PSA multiplied by the ratio of total PSA divided by the total concentration of free PSA the ratio of free SCINT-PSA divided by the total concentration of free PSA multiplied by total PSA or alternatively by:

the use of logistic regression analysis of the various measured parameters into receiver operating characteristics (ROC) analyses.

the use of various artificial intelligence approaches such as artificial neural networks.

According to a further aspect of the invention, it is preferentially applied to a subset of patient samples mainly characterized by moderately elevated levels of total or complexed PSA, i.e. concentrations of PSA where the diagnostic discrimination of cancer and noncancer conditions by total or complexed PSA alone is less reliable and in which the cancers detected are more likely to be organ-confined and eligible for curative treatments. Such an area is frequently defined as total PSA ranges from 3 or 4 to 20 µg/L but can be defined differently as regards both the lower limit (which can be even lower, e.g. 2.0 or 2.5 µg/L) or the higher limit (which can be even higher or lower, e.g. 8.0, 10, 12 or 15 µg/L).

According to still another aspect of the invention, the concentrations of SCINT-PSA or PSA-N alone or in combination with other measured parameters e.g. by using various ratios, logistic regression analysis or artificial intelligence approaches can also be used to identify sub-groups of the identified prostate cancer patients, more specifically those prostate cancers that are likely to remain indolent or progress slowly from those cancers that are likely to progress more aggressively. Other clinical applications of the invention may relate to the discrimination of pathologically organ-confined disease from disease stages with extraprostatic extension, either locally advanced or metastatic disease. Yet another clinical application of the invention may relate to the detection of early recurrence of cancer after curative treatment procedures, or to provide improved means in monitoring of therapeutic response at various stages of disease.

Different immunogen structures were used to develop monoclonal antibodies against different free PSA-forms; (i) affinity-purified PSA from LNCaP cells of which half the protein was recovered in mature single-chain form, and half was recovered in the −5 or −7 zymogen form. The second immunogen structure consisted of a 14 amino acid synthetic peptide including the pro-sequence of PSA and the seven first amino-terminal amino acids (APLILSRIVGGWEC) (SEQ ID NO:6) conjugated to KLH and BSA. Various screening methods were used to identify antibodies, which detect PSA isolated from LNCaP cells with different signal intensity than PSA from seminal plasma.

Characterization of the epitope groups of PSA in a 3-D model structure using antibodies binding to linear peptide sequences showed that the new 5H6 Mab mapped to the peptide sequence aa 225-237 which is very close to the previously characterized epitope of Mab E73. Mabs 4D4 and 5C3 were bound to peptide sequence 136-144. This is a previously unrecognized antigenic epitope on PSA which neighbors the internal cleavage site between Lys145 and Lys146, as well as the catalytically active site in the vicinity of the Mab 4D4 and Mab 5C3 epitopes. Mabs 4D4, 5C3, and 5H6 recognized free PSA and PSA-ACT complex with similar affinity, but did not recognize hK2.

Mabs 4D4 and 5C3 had affinity constants of $2.5 \times 10^9$ 1/M and $2.7 \times 10^9$ 1/M respectively for proPSA and intact forms of PSA. They recognized seminal plasma PSA significantly less than proPSA, and the amount of Mabs 4D4, 5C3 bound to fractions that predominantly (95%) contains internally cleaved PSA at Lys145-Lys146 was only 5% compared to the amount of antibody bound to pools which contained only intact PSA.

The invention will be described in more detail by the following experimental section.

Experimental Section

Methods and Materials

Reagents and Instrumentation

Freund's complete and incomplete adjuvants were obtained from Sigma Chemical Co. (St. Louis, Mo.). Cell culture 96-well plates were obtained from Nunc (Denmark), Roller bottles from Corning (NY) and Celline bioreactors from Integra (Germany). Optimem 1 with Glutamax-1 and HAT supplement (hypoxanthine, aminopterin and thymidine) are products of Life Technologies (Gibco BRL, Scotland). Heat inactivated fetal bovine serum (FBS) was from Hyclone (Logan, Utah). Sp 2/0 mouse myeloma cells were obtained from ATCC (Rockville, Md.). The synthetic −7 to +7 proPSA peptide was from Dr. Hans Lilja (University of Lund, Malmö, Sweden). The 1234 Delfia Plate fluorometer, Delfia Eu-labelling kit, microtitration plates coated with rabbit anti-mouse IgG, anti-PSA Mab H117, anti-PSA Mab 2E9 or streptavidin, Delfia Assay buffer, wash solution and enhancement solution were from PerkinElmer Life Sciences (Turku, Finland). HiTrap Protein G affinity column, Superose 12 HR 10/30 FPLC column for gelfiltration, PBE 94 Polybuffer exchanger and Polybuffer 96 for chromatofocusing were from Amersham Pharmacia Biotech AB (Uppsala, Sweden). Amino-terminal sequence analysis were done with an Applied Biosystems model 477A pulsed liquid sequencer connected to an online Applied Biosystems model 120A phenylthiohydantoin amino acid analyzer (Perkin Elmer, Norwalk, Conn.). Monoclonal antibodies 5A10, 2E9, 2H11, 3C1, 4H5 and 2C1 have previously been characterized. MAbs 66 and 10 were a kind gift of from Dr. O. Nilsson (CanAg Diagnostics, Goteborg, Sweden). MAbs H117, H179, H164 and HSO were obtained from Abbott (Abbott Laboratories, Abbott Park, Ill.). Antibody E73 was a kind gift from Dr. Elisabeth Paus (The Radium Hospital, Oslo, Norway).

Immunogens.

Three different immunogen structures were used in order to develop antibodies against free forms of PSA. LNCaP PSA had previously been purified with affinity chromatography from spent cell culture medium. About half of the protein was in mature one-chain form of PSA, and half was in the −5 or −7 zymogen form. The second immunogen structure consisted of a 14 amino acid synthetic peptide including the pro-sequence of PSA and the seven first amino acids from the amino-terminal sequence (APLILSRIVGGWEC) (SEQ ID NO:6). This peptide was coupled to KLH and BSA using the Imject Immunogen EDC Conjugation Kit (Pierce, Ill.). A third immunogen used was a mutated form of hK2, (fXahK2), in which two amino acids from the prosequence were changed. The point mutations in the prosequence render hK2 uncapable of autoactivation and cleavage of the prosequence. Second and third immunogen structures were used in immunizations in order to raise anti-proPSA antibodies. The immunizations and fusions with the peptide and hK2 were done essentially as described below for LNCaP PSA.

Immunizations.

Table 1 summarizes the immunizations that were made. Balb/c mice were immunized by intraperitoneal injection with varying amounts of the immunogen emulsified with Freund's complete adjuvant (Sigma). Booster doses were given at 3-4 week intervals. The total immunization times varied from 2 to 10 months. A final booster was given three days before the mice were killed. The splenic lymphoid cells were fused with myeloma cells Sp2/0 at a 1:1 ratio as described previously. The fused cells were harvested in cell culture 96-well plates in Optimem containing 20% fetal calf serum and HAT supplement.

Screening Methods.

Several different screening methods were used. Common for all the methods was that they were designed to recognize antibodies, which detect PSA produced by LNCaP cells somewhat differently than PSA obtained from seminal plasma. Four screening methods are presented in FIG. 1a-1d. In all the methods hybridoma supernatants were incubated overnight at +4° C. either in microtitration wells coated with rabbit anti-mouse antibody (methods 1, 2 and 4 or in microtitration wells coated with streptavidin and biotinylated synthetic peptide (method 3). After incubation, plates were washed four times. Detection of bound antibody was performed as described in FIG. 1a-d. For signal development, Delfia enhancement solution was used 200 µl/well. The signals were measured with a 1234 Delfia fluorometer.

Characterisation of Antibodies.

Purified proteins. LNCaP PSA was produced and purified as described by Väisänen et al. LNCaP proPSA and mature PSA forms were separated using chromatofocusing, which separates these forms based on their different pI values. The pH gradient was from 8.5 to 6 and buffers used were 0.025M ethanolamine-$CH_3COOH$ pH 8.5 and Polybuffer pH 6 (diluted 1:10). Chromatofocusing was done using 30 ml Polybuffer exchanger gel packed into C 10/40 column and ÄKTAexplorer 100 system (Amersham Pharmacia Biotech AB Uppsala, Sweden). The flow rate was 0.3 ml/min and 3.6 ml fractions were collected. Prior to fraction collecting 1/10 volume of 2M Tris-HCl pH 8 was added to each fraction tube. Each fraction was measured for PSA concentration using the Prostatus PSA free/total kit (PerkinElmer Life Sciences, Turku, Finland). Fractions containing PSA from one peak area were pooled and subjected to aminoterminal sequencing.

Separate pools of purified seminal plasma PSA were a generous gift from Dr. U-H Stenman. Pools A, B, C, D and E contain different amounts of internally cleaved PSA as described by Zhang et al. Pools A and B contain only intact PSA. Pools C and D contain intact form of PSA and PSA forms that have been internally cleaved at Arg85-Phe86 and Lys145-Lys146. Pool D contained also a minor part of PSA cleaved between Lys182-Ser183. Pool E contained mostly internally cleaved form Lys145-Lys146. The staining intensities in SDS-PAGE suggested that the amount of intact PSA in pools C, D and E was roughly 20%, 10% and less than 5%, respectively.

TABLE 1

Summary of immunizations and results from fusions.

| Fusion | Immunogen | Amount of immunogen (µg) | Number of boosters | Total immunisation time (months) | Used screening methods | PSA positive cell lines (%) | mAbs further characterised |
|---|---|---|---|---|---|---|---|
| 1 | LNCaPPSA | 30-60 | 3 | 3 | 1, 4 | 7 | 5F12 |
| 2 | LNCaPPSA | 30-60 | 3 | 4 | 1, 4 | 10 | 7C4, 5F7 |
| 3 | LNCaPPSA | 60-100 | 3 | 4 | 1, 4 | 10 | |
| 4 | LNCaPPSA | 60-100 | 4 | 7 | 2, 4 | 1 | |
| 5 | LNCaPPSA | 60-100 | 4 | 7 | 2, 4 | 16 | 4D4, 5C3, 5H6, 7G1 |
| 6 | LNCaPPSA | 30-60 | 4 | 8 | 1, 2, 3, 4 | 18 | |
| 7 | LNCaPPSA | 60-100 | 4 | 8 | 1, 2, 3, 4 | 19 | |
| 8 | LNCaPPSA | 30-60 | 4 | 10 | 4 | | |
| 9-16 | Peptide | 10-130 | 2-4 | 2-4 | 3, 4 | 0-1 | |
| 17-20 | fXahK2 | 35-60 | 3 | 3 | 4 | 0-1 | |

HK2 was produced with the baculovirus expression system and purified as described by Lövgren et al. Preparation and purification of PSA-ACT in vitro has been described earlier Epitope Mapping.

Previously characterized MAbs were used in sandwich assays in all possible combinations with the investigated MAbs to determine the binding sites on the PSA molecule.

Peptide Mapping.

Synthetic 15 mer peptides overlapping the whole PSA sequence were used for the determination of specific binding sites of antibodies that recognize continuous epitopes. Europium-labeled MAbs were incubated with biotinylated peptides attached to streptavidin plates as described by Piironen et al.

Specificity and Binding to Various PSA Forms.

Using a suitable partner antibody, the specificity of the new MAbs was determined using PSA, hK2 and PSA-ACT complex. In addition, binding to various PSA forms was determined using pools A, B, C, D and E of PSA purified from seminal plasma as described by Zhang et al., and using proPSA purified from LNCaP PSA as described by Väisänen et al.

Affinity of Mabs.

The affinity constants of Eu-labeled MAbs were determined as described previously earlier using 2E9 or H117 as capture antibodies and PSA purified from seminal plasma or purified hK2. The affinities were calculated using the Scatchard method.

Immunoassays.

A two-site immunoassay protocol was developed for the specific determination of free SCINT-PSA. This design used (i) Mab 5C3 that mapped to an epitope containing the peptide sequence aa 136-144 in PSA, which (ii) was combined with a previously characterized free-specific Mab (5A10) which was mapped to an epitope containing peptide sequence aa 84-91. Biotinylated preparations of Mab 5C3 were immobilised to streptavidin coated plates using 200 ng Mab in 200 µL Assay Buffer in a 60 min incubation at room temperature. Following a wash step to remove unbound biotinylated Mab, 50 µL standard or sample was added per well followed by 100 µL Delfia buffer and incubated at room temperature for 60 min under continuous shaking After washing twice, 100 µL Delfia assay buffer containing 100 ng Eu-labelled Mab 5A10 was added per well and incubated for 60 min at room temperature under continuous shaking Following a final wash (6×), 200 µL per well of Delfia Enhancement solution was added. After shaking for 5 min the signal was measured in a 1232 Delfia Plate fluorimeter. The concentrations of the unknown samples were calculated from a standard series (0.05 to 200 µg/L PSA) of recombinant baculovirus produced proPSA.

Other immunoassays used were: Delfia ProStatus F/T PSA (from Perkin-Elmer, Wallac, Turku, Finland), and an investigational assay for hK2 [Becker et al. *Clin Chem* 2000; 46: 198-206].

Clinical Study Population

The study population consisted of two hundred and ninetyone (291) men, aged 51-66 years, participating in a population based prostate cancer screening study in the area of Gothenburg, Sweden, and initially presenting with a concentration of total PSA>3 µg/L [Becker et al. *Urology* 2000; 55:694-699]. Prior to performing DRE, TRUS and a TRUS guided sextant biopsy, additional serum and EDTA plasma samples were obtained. After clotting (serum) and centrifugation performed within 3 hours after venipuncture, the samples were frozen at 70° C. For this study we used the EDTA plasma sample which was thawed immediately before performing the immunoassays. The sextant biopsies revealed prostate cancer in 79 men out of the 291 tested.

Statistical Analyses.

Descriptive statistics were given as medians, upper and lower quartiles (25 and 75 percentiles). Mann-Whitney non-parametric tests were performed to test whether there were statistically significant differences (p<0.05) in PSA-T, PSA-F, free SCINT-PSA, PSA-N, hK2, hK2/PSA-F, PSA-F/PSA-T, free SCINT-PSA/PSA-F, free SCINT-PSA/PSA-T, PSA-N /PSA-T, (free SCINT-PSA/PSA-F)×PSA-T, (free SCINT-PSA/PSA-F)×PSA-T×hK2, (free SCINT-PSA/PSA-F)/ (PSA-F/PSA-T) between the two groups of patients (cancers and noncancers). This analysis was performed both on the total patient material as well as for various sub-groups selected on the basis of the PSA-T range.

Results

Immunizations and Screenings

Our aim was to find novel antibodies that would recognize various molecular forms of PSA specifically present in cancer. Antibodies that gave very high positive signal or recognized the tested PSA forms from LNCaP differently compared to PSA from seminal fluid were produced and characterized further. Table 1 summarizes immunizations that were made, number of PSA positive cell lines and MAbs that were further characterized from each fusion. All finally characterized MAbs were from fusions where LNCaP PSA was used as an immunogen. Some cell lines from peptide fusions were positive for the synthetic peptide, but further testing showed, that antibodies did not recognize the entire PSA molecule. Also, some anti-PSA positive cell lines were obtained from fXahK2 fusions, but these antibodies could not distinguish LNCaP PSA from seminal plasma PSA, and were therefore not characterized further.

Antibody Characteristics

Epitope mapping. Novel MAbs were tested with various antibody combinations to define their binding site on the PSA molecule. Based on the results, a 2-D epitope map was constructed (FIG. 2). The binding sites of novel anti-PSA MAbs are presented in relation to previously characterized MAbs.

Different binding regions of 83 anti-PSA monoclonal antibodies have been described by Paus et al. in the ISOBM study, where binding regions from 1 to 6 are mapped in a 2-D and 3-D model. The binding regions of novel anti-PSA antibodies were compared to binding sites of previously characterized MAbs.

5F12 mapped to group I free-PSA specific antibodies that bound to same epitope as previously characterized MAb 5A10 (#25) in the ISOBM study. Interestingly, 5F12 also blocked MAb PSA10 (#72) binding, which belongs to antibody group 3a. 7G1 was bound to an epitope close to HSO (#57) and PSA10 in antibody group 3a. 7G1 was also somewhat inhibited by antibody 2H11 (#41), which belongs to group 5b antibodies. Also 5F7 and 5H6 were bound to an area overlapping with MAbs HSO and PSA10 binding sites. Further, 7C4, 4D4 and 5C3 bound to an area close to the binding site(s) of Mabs H164, HSO and 2H11, which is located near antibody group 5b.

Peptide mapping. Three of seven tested MAbs bound to linear biotinylated 15 mer peptides overlapping the entire PSA sequence (table 1).

4D4 and 5C3 antibodies were both bound to 15 mer peptide sequences 130 ASGWGSIEPEEFLTP 144 (SEQ ID NO:1)

and 136 SIEPEEFTLTPKKLQC 149 (SEQ ID NO:2). The common amino acid sequence for these two overlapping 15 mer peptides is sequence 136 SIEPEEFLTP 144 (SEQ ID NO:3). A common internal PSA cleavage site is located between amino acids Lys145 and Lys146 which renders PSA inactive.

5H6 was bound to the C-terminal peptide of PSA (225 YRKWIKDTIVANP 237; SEQ ID NO:4). Another antibody (E73) has been characterized to bind close to the C-terminal part of PSA molecule (data not shown). MAb E73 was bound to the 15 mer peptide (215 RPSLYTKVVHYRKWI 229; SEQ ID NO:5) which is partially overlapping to that recognized by 5H6.

Results from peptide binding studies were combined with the data presented by Piironen et al. to create a 3-D epitope map showing seven independent antigenic domains on the PSA moiety (FIG. 3).

Specificity of the Mabs. 5F12 was a free PSA specific antibody. 7C4, 4D4, 5C3, 5F7 and 5H6 recognized free PSA and PSA-ACT complex with similar affinity, but did not recognize hK2. 7G1 recognized free PSA, PSA complexed with ACT, and hK2 with similar affinity.

Binding to various PSA forms. Binding of new MAbs to different PSA forms was tested using sandwich assay formats with different previously characterized capture antibodies and new MAbs as tracers. Binding was studied to mature intact PSA, compared to mature internally cleaved PSA forms, and to proPSA. Significant differences in binding to various PSA isoforms was found only for MAbs 4D4 and 5C3.

Clones 4D4 and 5C3 recognized seminal plasma PSA with lower signal intensity than proPSA using screening method 4. These antibodies were further tested with different pools of PSA isolated from seminal plasma that contained various amounts of internally cleaved PSA, i.e. two- or multi-chain forms. There was only 5% of antibody (4D4, 5C3) bound to pool E that predominantly ≈05%) contains PSA that is internally cleaved between Lys145-Lys146 compared to the amount of antibody (set at 100%) bound to pools A and B, which contained only intact single-chain PSA. Therefore, these antibodies may only recognize PSA forms where there is no internal cleavage at Lys145-Lys146, such as in LNCaP PSA, which was used as an immunogen. FIG. 4a-4c illustrate the reactivity of different antibodies with pools A-E of seminal plasma PSA. Antibodies were tested in sandwich assay format that used H117 coated plates or streptavidin plates coated with biotinylated 5A10 as capture. Antibodies are designated according to different binding regions illustrated in the ISOBM study.

Affinity of Mabs. Affinity constants of MAbs are listed in table 2. All the characterized MAbs showed high affinity for seminal plasma PSA (Ka$>1\times10^9$ 1/M). 7G1 had very high affinity for both PSA and hK2 (Ka=$2\times10^{10}$ 1/M). 4D4 and 5C3 had affinity constants of $2.5\times10^9$ 1/M and $2.7\times10^9$ 1/M respectively for proPSA and intact PSA forms. In addition, 4D4 and 5C3 were tested for their affinity for pools of seminal plasma PSA that contain internally cleaved forms (pools C, D and E). The affinity constants of these two MAbs decreased with increasing amounts of internally cleaved PSA forms. Affinity of 4D4 and 5C3 for pool E PSA could not be determined using the Scatchard method due to very low affinity (data not shown).

TABLE 2

Summary of antibody characteristics.

| Antibody | Specificity* | Affinity Mab-Eu l/M | Binding to peptide sequence |
|---|---|---|---|
| 5F12 | PSA-F | n.d | negative |
| 5F7 | PSA-T | $6.4 \times 10^9$ | negative |
| 7C4 | PSA-T | $1.8 \times 10^9$ | negative |
| 4D4 | PSA-T | $2.5 \times 10^9$ | 135-144 |
| 5C3 | PSA-T | $2.7 \times 10^9$ | 135-144 |
| 5H6 | PSA-T | $4.4 \times 10^9$ | 225-237 |
| 7G1 | PSA-T + hK2 | $2 \times 10^{10}$ | negative |

*PSA-F = free PSA, PSA-T = free PSA and PSA-ACT complex

SCINT-PSA Immunoassay Performance

A typical standard curve is shown in FIG. 5. The analytical detection limit (background+2 SD) was ≦0.05 μg/L and the standard curve was linear up to the highest standard point used (50 μg/L). Within and between assay variation were below 6 and 8 percent respectively over the concentration range from 0.2 to 50 μg/L.

Measurement of Free SCINT-PSA, PSA-F, PSA-T and hK2 in Study Population Sera

The median concentrations (and 25- and 75-percentiles) of the different measured parameters free SCINT-PSA, PSA-F, PSA-T and hK2 as well as combinations of these into various ratios or algorithms are given in Table 1 to 3 for the whole study population, for patients with PSA-T≧10 and for PSA-T<5. Statistical analysis between cancers and noncancers were performed using the nonparametric Mann-Whitney U-test.

TABLE 3

Discrimination of cancers (N = 197) and non-cancers (N = 79) using single or combined parameters without restrictions as to the concentrations of PSA-T. Statistical analysis was performed using the non-parametric Mann-Whitney-U test. Statistical significance (p < 0.05) is shown in bold characters, borderline statistical significance (p 0.05-0.1) in italics.

| Parameter | Non-cancers Median (25-, 75-% iles) | Cancers Median (25-, 75-% iles) | Mann-Whitney-U p-value |
|---|---|---|---|
| PSA-T | 4.01 (3.01, 5.71) | 5.25 (3.79, 11.8) | <0.0001 |
| PSA-F | 0.88 (0.57, 1.37) | 0.94 (0.58, 1.65) | 0.435 |
| free SCINT-PSA | 0.43 (0.29, 0.59) | 0.48 (0.35, 0.85) | 0.0063 |
| PSA-N (PSA-F - free SCINT-PSA) | 0.41 (0.23, 0.81) | 0.34 (0.16, 0.61) | 0.0271 |
| hK2 | 0.044 (0.031, 0.066) | 0.060 (0.033, 0.101) | 0.0018 |
| hK2/PSA-F | 0.052 (0.032, 0.077) | 0.069 (0.043, 0.115) | 0.0027 |
| PSA-F/PSA-T | 0.20 (0.16, 0.28) | 0.15 (0. 10, 0.18) | <0.0001 |
| free SCINT-PSA/PSA-F | 0.47 (0.39, 0.59) | 0.59 (0.48, 0.78) | <0.0001 |
| free SCINT-PSA/PSA-T | 0.10 (0.076, 0.134) | 0.084 (0.065, 0.115) | 0.0055 |
| PSA-N/PSA-T | 0.104 (0.067, 0.164) | 0.055 (0.024, 0.095) | <0.0001 |

TABLE 3-continued

Discrimination of cancers (N = 197) and non-cancers (N = 79) using single or combined parameters without restrictions as to the concentrations of PSA-T. Statistical analysis was performed using the non-parametric Mann-Whitney-U test. Statistical significance (p < 0.05) is shown in bold characters, borderline statistical significance (p 0.05-0.1) in italics.

| Parameter | Non-cancers Median (25-, 75-% iles) | Cancers Median (25-, 75-% iles) | Mann-Whitney-U p-value |
|---|---|---|---|
| (free SCINT-PSA/PSA-F) × PSA-T | 2.03 (1.33, 2.89) | 2.80 (2.08, 7.06) | <0.0001 |
| (free SCINT-PSA/PSA-F) × PSA-T × hK2 | 0.094 (0.055, 0.167) | 0.202 (0.115, 0.457) | <0.0001 |
| (free SCINT-PSA/PSA-F)/(PSA-F/PSA-T) | 2.31 (1.43, 3.51) | 4.23 (2.58, 6.29) | <0.0001 |

TABLE 4

Discrimination of cancers (N = 54) and non-cancers (N = 187) using single or combined parameters in the PSA-T range below or equal to 10 μg/L. Statistical analysis was performed using the non-parametric Mann-Whitney-U test. Statistical significance (p < 0.05) is shown in bold characters, borderline statistical significance (p 0.05-0.1) in italics.

| Parameter | Non-cancers Median (25-, 75-% iles) | Cancers Median (25-, 75-% iles) | Mann-Whitney-U p-value |
|---|---|---|---|
| PSA-T | 3.92 (2.98, 5.47) | 4.07 (3.48, 5.28) | 0.35 |
| PSA-F | 0.83 (0.56, 1.29) | 0.66 (0.48, 1.02) | *0.058* |
| free SCINT-PSA | 0.42 (0.28, 0.57) | 0.38 (0.28, 0.55) | 0.023 |
| PSA-N (PSA-F - free SCINT-PSA) | 0.39 (0.23, 0.73) | 0.27 (0.14, 0.49) | 0.0043 |
| hK2 | 0.043 (0.030, 0.064) | 0.048 (0.029, 0.065) | 0.448 |
| hK2/PSA-F | 0.054 (0.034, 0.077) | 0.067 (0.042, 0.101) | 0.024 |
| PSA-F/PSA-T | 0.21 (0.16, 0.28) | 0.16 (0.14, 0.19) | 0.0002 |
| free SCINT-PSA/PSA-F | 0.47 (0.39, 0.59) | 0.58 (0.45, 0.76) | 0.0018 |
| free SCINT-PSA/PSA-T | 0.10 (0.079, 0.136) | 0.096 (0.071, 0.118) | 0.253 |
| PSA-N/PSA-T | 0.103 (0.068, 0.167) | 0.071 (0.039, 0.107) | 0.0002 |
| (free SCINT-PSA/PSA-F) × PSA-T | 1.94 (1.29, 2.70) | 2.36 (1.90, 2.96) | 0.0035 |
| (free SCINT-PSA/PSA-F) × PSA-T × hK2 | 0.092 (0.087, 0.158) | 0.158 (0.087, 0.266) | 0.0004 |
| (free SCINT-PSA/PSA-F)/(PSA-F/PSA-T) | 2.32 (1.42, 3.50) | 3.42 (2.22, 5.58) | <0.0001 |

TABLE 5

Discrimination of cancers (N = 38) and non-cancers (N = 128) using single or combined parameters in the PSA-T range below or equal to 5 μg/L. Statistical analysis was performed using the non-parametric Mann-Whitney-U test. Statistical significance (p < 0.05) is shown in bold characters, borderline statistical significance (p 0.05-0.1) in italics.

| Parameter | Non-cancers Median (25-, 75-% iles) | Cancers Median (25-, 75-% iles) | Mann-Whitney-U p-value |
|---|---|---|---|
| PSA-T | 3.38 (2.58, 3.99) | 3.72 (3.18, 4.12) | *0.057* |
| PSA-F | 0.65 (0.48, 0.92) | 0.58 (0.42, 0.72) | *0.063* |
| free SCINT-PSA | 0.33 (0.23, 0.45) | 0.35 (0.24, 0.42) | *0.063* |
| PSA-N (PSA-F - free SCINT-PSA) | 0.32 (0.20, 0.52) | 0.20 (0.13, 0.35) | 0.0055 |
| hK2 | 0.039 (0.025, 0.051) | 0.042 (0.029, 0.060) | 0.589 |
| hK2/PSA-F | 0.059 (0.036, 0.082) | 0.076 (0,047, 0,117) | *0.086* |
| PSA-F/PSA-T | 0.20 (0.16, 0.28) | 0.16 (0.13, 0.19) | <0.0001 |
| free SCINT-PSA/PSA-F | 0.49 (0.41, 0.60) | 0.59 (0.50, 0.73) | 0.0012 |
| free SCINT-PSA/PSA-T | 0.10 (0.077, 0.141) | 0.094 (0.075, 0.118) | 0.1688 |
| PSA-N/PSA-T | 0.097 (0.067, 0.159) | 0.063 (0.039, 0.095) | 0.0001 |
| (free SCINT-PSA/PSA-F) × PSA-T | 1.58 (1.11, 2.12) | 2.12 (1.73, 2.59) | <0.0001 |
| (free SCINT-PSA/PSA-F) × PSA-T × hK2 | 0.078 (0.049, 0.146) | 0.158 (0.090, 0.248) | 0.0023 |
| (free SCINT-PSA/PSA-F)/(PSA-F/PSA-T) | 2.40 (1.44, 3.57) | 3.71 (2.62, 5.84) | <0.0001 |

Statistical analysis of the immunoassay measurements of the whole clinical study material (i.e. no PSA-T restrictions as shown in Table 3), reveals that the levels of both PSA-T (p<0.0001), free SCINT-PSA (p=0.0063) and of hK2 (p=0.018) as well as the single parameter PSA-N (p=0.0271) were significantly different for the cancer compared to the noncancer group whereas PSA-F (p=0.435) could not differentiate between the two groups. All two-parameters ratios, most notably PSA-F/PSA-T, free SCINT-PSA/PSA-F and PSA-N/PSA-T (all p<0.0001), discriminated well between the two groups. The proportion (medians) of free SCINT-PSA relative to PSA-F was 47 percent in noncancers compared to 59 percent in cancers (p<0.0001). The three- or four-parameter algorithms also separated cancers and noncancers with high statistical significance.

In the PSA-T range≦10 μg/L (Table 4) of the single parameters only free SCINT-PSA and PSA-N discriminated between cancers and noncancers. Especially noteworthy is the fact that median concentrations of PSA-N was 0.39 μg/L in noncancers and 0.27 μg/L in cancers (p=0.0043). Of the two-parameter ratios, PSA-F/PSA-T (p=0.0002), PSA-N/PSA-T (p=0.0002), free SCINT-PSA/PSA-F (p=0.0018) discriminated well between the two clinical groups as did all the three- and four parameter algorithms. The proportion (medians) of free SCINT-PSA relative to PSA-F was 47 percent in noncancers compared to 58 percent in cancers (p=0.0018).

In the PSA-T range≦5 μg/L (Table 5) of the single parameters only PSA-N discriminated between cancers and noncancers. Median concentrations of PSA-N was 0.32 μg/L in noncancers and 0.20 μg/L in cancers (p=0.0055). Of the two-parameter ratios, PSA-F/PSA-T (p<0.0001), PSA-N/PSA-T (p=0.0001), free SCINT-PSA/PSA-F (p=0.0012) discriminated well between the two clinical groups as did all the three- and four parameter algorithms. Also in this PSA-T range the proportion (medians) of free SCINT-PSA relative to PSA-F was very similar to that of the whole study material i.e. 49 percent in noncancers compared to 59 percent in cancers.

DISCUSSION AND CONCLUSIONS

One objective of the present study was to produce anti-PSA antibodies against PSA forms produced by metastatic cancer cell line, LNCaP, and to compare these antibodies to a large set of previously characterized antibodies obtained from immunizations with seminal plasma PSA. We wanted to obtain novel anti-PSA antibodies against different isoforms of free PSA in order to develop specific immunoassays for their detection. One aim was to develop anti-proPSA antibodies. In addition to immunizations using LNCaP PSA as an immunogen, a synthetic peptide consisting of amino acids −7 to +7 was conjugated to carrier protein and used in immunizations. Also a mutated form of hK2, fXahK2, was used in immunizations. This form contains a mutated propeptide that prevents the autoactivation of the zymogen-protein which results from the loss of the propeptid. Since hK2 and PSA have 79% amino acid identity, anti-PSA specific antibodies were expected to be generated from fXahK2 fusions.

About 50 percent of the purified LNCaP PSA consisted of single-chain mature form and to about 50 percent of zymogen form. Eight LNCaP PSA fusions generated more than thousand wells that were positive for PSA. 125 cell lines were selected, grown and tested with several different methods. Most of the antibody characteristics were very similar to the previously characterized anti-PSA antibodies. However, three novel antibodies with previously unknown epitope characteristics were obtained. Two novel antibodies (4D4 and 5C3) were bound to an epitope adjacent to the most common internal peptide cleavage site in PSA ($Lys_{145}$-$Lys_{146}$) and one antibody (5H6) was bound to the C-terminal peptide of the protein. Synthetic peptide fusions and fXahK2 fusions did not produce any novel anti-PSA antibodies.

4D4 and 5C3 bound to linear peptide sequence adjacent to Lys145-Lys146 cleavage site. These antibodies were very similar in their PSA isoform specificity and affinity even though they were from different clones. They did not recognize hK2. 4D4 and 5C3 inhibited the activity of PSA towards chromogenic peptide substrate (data not shown), which was expected since the catalytically active site of PSA has been mapped next to the internal cleavage site Lys145-Lys146 (FIG. 3). When these antibodies were tested with seminal plasma PSA pools that contained different amounts of internally cleaved PSA forms, it could be seen that these antibodies did not recognize PSA that was internally cleaved between Lys145 and Lys146. Internal cleavage of PSA at Lys145-Lys146 site results in the loss of enzymatic activity. Thus, 4D4 and 5C3 do not recognize PSA that is inactive due to internal cleavage at Lys145-Lys146.

5H6, another novel antibody was bound to the C-terminal peptide of lasts 15 amino acids on the PSA molecule. This peptide is helical in native form and is located on the surface of the molecule. Amino acid 234 in PSA molecule is valine, but in hK2 it is alanine Due to this difference in one amino acid, this antibody does not recognize hK2. Another antibody, E73 from Dr. E. Paus was also mapped to the C-terminal part of PSA, but the peptide sequence is only partly overlapping with the 5H6 binding site.

An immunoassay was constructed that used 5H6 as a tracer antibody. The idea of this assay was to study changes in the C-terminal part of PSA. Since 5H6 binds to the C-terminal peptide of PSA, it was thought that cleavage of amino acids at C-terminus might result in decrease of 5H6 binding to PSA. Väisänen et al. reported that mature LNCaP PSA grown with serum is inactive for unknown reason. Also Corey et al. reported similar results, showing that part of the inactive fraction of PSA could be activated with trypsin, but part remained in inactive form. Cleavage of amino acids at the C-terminus of PSA could change the conformation of the protein and possible render PSA inactive. LNCaP PSA forms from spent cell culture medium of LNCaP cells grown with serum or without serum were separated after affinity purification using chromatofocusing into proform and mature form of the protein. Different LNCaP PSA forms were tested with an immunoassay that used H117 as capture antibody and 5H6 as tracer antibody. We wanted to see whether these different LNCaP PSA forms differ in their C-terminal amino acid sequence. Immunoassay with 5H6 did not shown difference between these different PSA forms (data not shown).

Elevated serum PSA concentration may result from various urological problems other than prostate cancer and thus PSA is not cancer specific. However, the proportion of PSA-F to PSA-ACT complex in serum has been shown to be significantly higher in BPH than in prostate cancer [Stenman et al. *Cancer Res* 1991; 51:222-226, Christensson et al. *J Urol* 1993; 150:100-5]. The mechanisms that result into the increased fraction of serum free PSA in BPH are not known. Björk et al. [Björk et al. *Urology* 1994; 43:427-34] reported lack of ACT production in PSA-containing BPH nodules in contrast to cancerous tissues, where production of both PSA and ACT could be detected. This could lead to more PSA-ACT complex formation in cancer, and thus explain the difference in the amount of free PSA in BPH and prostate cancer. However, Jung et al. [Jung et al. *Clin Chem* 2000; 46:47-54] demonstrated, that the amounts of different forms of PSA in prostatic tissue do not correlate with amounts or ratios of different PSA forms in serum. Thus, the isoform patterns seen in serum might not be a simple reflection of PSA isoform patterns in tissue. Instead, release of different proportions of enzymatically active or inactive forms of free PSA from neoplastic and benign cells might result in the difference of free-to-total PSA ratio in PCa and BPH.

There have been controversial reports about the nature of free PSA in serum. Zymogen form of PSA starting at amino acid −4 in serum of prostate cancer patients was reported by Mikolajczyk et al. [Mikolajczyk et al. *Urology* 1997; 50:710-4]. LNCaP cells have been shown to produce proforms of PSA starting at amino acid −7 or −5. These proforms have high isoelectric pI values that according to Väisänen et al. disappeared after incubation with hK2. These high pI points have also been found in serum of patients with advanced prostate cancer, but not with patients with BPH [Huber et al. *Prostate* 1995; 27:212-9] Noldus et al. [Noldus et al. *J Urol* 1997; 158:1606-9] however, did not detect any zymogen forms in high-grade prostate cancer patient's sera. Their purification methods did not exclude hK2, which could possibly cleave proPSA into the mature form during purification steps.

Answers to the different forms of free PSA could add new discriminatory information to the diagnostics of prostate cancer. An anti-proPSA antibody would enable specific and sensitive measurement of the zymogen forms of the protein. Despite the high immunogenic nature of the LNCaP PSA, we could not find antibodies specific or even with a stronger preference for the zymogen form of PSA.

There could be many reasons for not obtaining anti-proPSA antibodies. It has been shown that the PSA prosequence of mouse kallikreins is similar to kallikrein prosequences in human [Fukushima et al. *Biochemistry* 1985; 24:8037-43]. This could mean, that the propeptide is not immunogenic in mice. Also, due to the homology, mouse kallikreins might be able to conceivably cleave the human proPSA to mature PSA, resulting in the loss of prosequence. Additionally, the orientation of the prosequence in the PSA molecule is not known and it could be partly buried.

Characterization of various forms of free PSA from seminal plasma and prostate tissue has been one approach in understanding different molecular forms of free PSA and their relevance in different prostatic diseases. One explanation for the inactive free PSA forms are internally cleaved forms of PSA. Seminal plasma PSA has been shown to contain ~30% internally cleaved PSA, where the most common internal cleavage site is at Lys145-Lys146 [Christensson et al. *Eur J Biochem* 1990; 194: 755-63] Noldus et al [Noldus et al. *J Urol* 1997; 158:1606-9] detected this internally cleaved PSA form in high-grade prostate cancer patient's sera. Charrier et al. [Charrier et al. *Electrophoresis* 1999; 20:1075-81] used two-dimensional electrophoresis in comparing pattern of PSA forms in BPH and PCa sera. They demonstrated that BPH sera contain more cleaved forms of free PSA than PCa sera. Internal cleavage sites have also been identified between Arg85-Phe86 and Lys182-Ser183 [Zhang et al. Clin Chem 1995; 41:1567-73, Watt et al. *Proc Natl Acad Sci USA* 1986; 83:3166-70]. A recently characterized novel form of PSA, "B-PSA", that was isolated from benign transition zone tissue of BPH patients contains the internal cleavage site at Lys182-Ser183 [Mikolajczyk et al. *Urology* 2000; 55:41-5] In BPH nodule fluids Chen et al. [Chen et al. *J Urol* 1997; 157:2166-70] reported PSA forms with internal cleavage sites at His54-Ser55, Phe57-His58, Lys145-Lys146 and Lys146-Leu147. It is not known, whether cleavages at these other sites except Lys145-Lys146 inactivate PSA.

Zhang et al. [Zhang et al. *Clin Chem* 1995; 41:1567-73] reported an inactive mature unclipped form of PSA in seminal fluid that could not form complex with ACT. This intact, inactive PSA has been found also in serum [Mikolajczyk et al. *Urology* 1997; 50:710-4, Noldus et al. *J Urol* 1997:158-1606-9, Qian et al. *Clin Chem* 1997; 43:352-9] and in spent medium of LNCaP cells [Väisänen et al. *Prostate Cancer and Prostatic Diseases* 1999; 6:1-7, Corey et al. *Prostate* 1998; 35: 135-43]. At present there is no explanation for this inactive form of PSA.

There are separate antigenic areas on the PSA molecule (FIG. 3). The presence of these areas might lower the possibility of obtaining antibodies against less immunogenic areas. In this study, however, antibodies against two new previously unrecognized epitopes were found Employing the novel and unique high affinity 5C3 or 4D4 Mabs described we were able to construct a simple and highly sensitive assay for free SCINT-PSA. These were used primarily as the detector antibodies with the free-PSA specific capture Mab 5A10. Since the two tracer Mabs in our hands behaved similarly we continued with only one of them, Mab 5C3. As evident from the epitope map (FIG. 2) Mabs 5C3 and 4D4 can easily be combined with other total PSA specific antibodies thus providing assays for complexed and free forms of SCINT-PSA.

Since free SCINT PSA by our definition consitute a subfraction of PSA-F, we could easily obtained the free nicked PSA (PSA-N) concentration by subtracting the free SCINT PSA level from that measured by a free PSA assay. This calculated parameter was shown to be a valuable parameter especially in forming the ratio PSA-N/PSA-T (or vice versa) to discriminate cancers from noncancers. It is evident from the 2-D epitope map (FIG. 2) that a direct measurement of nicked PSA can be constructed by using a preblocking step e.g. by Mab 5C3 and/or 4D4 whereby intact PSA, i.e. SCINT PSA is prevented, i.e. blocked, from further participation in the immunodetection. Of the selected sandwiching pair of antibodies one antibody (e.g. 2C1) would be on the basis that it recognizes an epitope overlapping the 5C3 and 4D4 specific epitope, and the other any other PSA antibody capable of good sandwich formation.

As seen from analyzing the clinical samples, a screening cohort, both free SCINT-PSA and PSA-N were both able alone or in a number of different combinations to discriminate in a highly significant manner between cancers and noncancers both for the whole cohort but also in the diagnostically difficult so called gray zone area of low ($\leq 5$ μg/L) or intermediate ($\leq 10$ μg/L) concentrations of PSA-T.

The combination of free SCINT-PSA and PSA-N with measurement of other forms of PSA or hK2 can naturally also be accomplished in other ways than forming ratios or other mathematical algorithms but also through combination by logistic regression. Combinations by logistic regression frequently provide even better discrimination than ratios calculated from the individual measurements from each patient. As combination through logistic regression, unlike the combination obtained through formation of ratios, does not provide a continuous variable, cut-off limits are not possible to define in these cases. Logistic regression analysis is instrumental in providing the basis for various "risk analysis systems that can provide medical decision support". Other examples of such data handling systems are also: artificial neural networks (ANN), neuro fuzzy networks (NFN), multilayer perceptron (MLP), learning vector quantization (LVQ) [Freeman J A et al., In: Neural Networks: Algorithms, Applications and Programming Techniques, Addison-Wesley Publishing Company 1991; Zadeh L A Information and Control, 1965, 8:338-353; Zadeh L A, IEEE Trans. on Systems, Man and Cybernetics 1973, 3:28-44; Gersho A et al., In: Vector Quantization and Signal Compression, Kluywer Academic Publishers, Boston, Dordrecht, London 1992; Hassoun M. H., Fundamentals of Artificial Neural Networks, The MIT Press, Cambridge, Mass., London 1995]

The invention claimed is:

1. An isolated monoclonal antibody, wherein said monoclonal antibody binds with high affinity to both mature and zymogen forms of native human single-chain intact prostate specific antigen (SCINT PSA) and said monoclonal antibody does not bind to a native nicked PSA (PSA-N), characterized in that said monoclonal antibody is obtained through immunization with an uncleaved form of prostate specific antigen (SCINT PSA), is selected by its differential binding to the intact and internally cleaved forms, wherein said SCINT PSA is prostate specific antigen (PSA) not internally cleaved between amino acids lysine 145 and lysine 146, wherein said PSA-N has been formed by internal peptide bond cleavage(s)

of SCINT PSA resulting in two-chain or multi-chain PSA and wherein the cleavage of PSA-N has occurred between amino acids lysine 145 and lysine 146 of the PSA.

2. An immunoassay for quantitative determination in a sample of both mature and zymogen forms of native human single-chain intact prostate specific antigen (SCINT PSA), or alternatively native nicked prostate specific antigen (PSA) forms (PSA-N), wherein said intact PSA (SCINT PSA) is not internally cleaved between amino acids lysine 145 and lysine 146, wherein said PSA-N has been formed by internal cleavage(s) of SCINT PSA resulting in two-chain or multi-chain prostate specific antigen (PSA) forms, and wherein said PSA, SCINT PSA or PSA-N occurs in free form, complexed form or both free and complexed forms which immunoassay comprises:

(a) contacting a sample with a first monoclonal antibody that binds with high affinity to said native SCINT PSA and does not bind to said native PSA-N and wherein the cleavage of PSA-N has occurred between amino acids lysine 145 and lysine 146 of the PSA (b) contacting the sample with a second monoclonal antibody, wherein the second monoclonal antibody is selected from the group consisting of a monoclonal antibody that binds with high affinity to free prostate specific antigen (PSA-F) and a monoclonal antibody that binds with high affinity to both PSA-F and complexed PSA; and (c) determining the amount of SCINT PSA in the sample.

3. The immunoassay according to claim 2, wherein the second monoclonal antibody is labeled.

4. The method of clam 2, wherein the second monoclonal antibody binds with high affinity to PSA-F and the amount of free SCINT-PSA in the sample is determined.

5. The method of claim 2, wherein the second monoclonal antibody binds with high affinity to both PSA-F and complexed PSA and the amount of free and complexed SCINT-PSA in the sample is determined.

6. The method of claim 4 which further comprises:

(d) determining the amount of PSA-F in the sample; and (e) determining the difference between the amount of free SCINT PSA and the amount of PSA-F to determine the amount of PSA-N in the sample.

* * * * *